United States Patent
Suenaga et al.

(10) Patent No.: US 11,946,924 B2
(45) Date of Patent: Apr. 2, 2024

(54) CROSSLINKED FLUOROPOLYMER RESIN AND CONTROL METHOD FOR SAME

(71) Applicant: Hitachi Metals, Ltd., Tokyo (JP)

(72) Inventors: Kazufumi Suenaga, Tokyo (JP); Koki Hirano, Tokyo (JP); Kenta Kimura, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 465 days.

(21) Appl. No.: 17/152,485

(22) Filed: Jan. 19, 2021

(65) Prior Publication Data

US 2021/0231636 A1    Jul. 29, 2021

(30) Foreign Application Priority Data

Jan. 24, 2020    (JP) ................. 2020-010430

(51) Int. Cl.
*G01N 21/65*    (2006.01)
*C08J 3/24*    (2006.01)
*G01N 23/2055*    (2018.01)
*G01N 33/44*    (2006.01)

(52) U.S. Cl.
CPC .......... *G01N 33/442* (2013.01); *G01N 21/65* (2013.01); *G01N 23/2055* (2013.01); *C08J 3/24* (2013.01); *C08J 2327/18* (2013.01); *G01N 2201/06113* (2013.01); *G01N 2223/0566* (2013.01); *G01N 2223/60* (2013.01)

(58) Field of Classification Search
CPC .... G01N 21/65; G01N 23/20; G01N 23/2055; G01N 33/442; C08J 3/24; C08J 3/247; C08J 2327/12; C08J 2327/18
See application file for complete search history.

(56) References Cited

U.S. PATENT DOCUMENTS

| | | | | |
|---|---|---|---|---|
| 6,307,625 B1 * | 10/2001 | Sharts | ................... | G01N 21/65 |
| | | | | 356/301 |
| 7,173,094 B2 * | 2/2007 | Morimoto | ................ | C08K 5/14 |
| | | | | 525/326.3 |
| 2017/0158848 A1 | 6/2017 | Kawahara et al. | | |

FOREIGN PATENT DOCUMENTS

| | | | | |
|---|---|---|---|---|
| JP | 10-38807 A | * | 2/1998 | ............. G01N 21/65 |
| JP | 2003-253007 A | * | 9/2003 | ................ C08J 3/28 |
| JP | 2012-197347 A | * | 10/2012 | ................ C08J 7/00 |
| JP | 2018-171557 A | | 11/2018 | |
| WO | 2015/190597 A1 | | 12/2015 | |

(Continued)

OTHER PUBLICATIONS

JP 2012-197347 A (Oct. 18, 2012); machine translation. (Year: 2012).*

(Continued)

*Primary Examiner* — Rip A Lee
(74) *Attorney, Agent, or Firm* — McGinn I.P. Law Group, PLLC.

(57) ABSTRACT

A crosslinked fluoropolymer resin is configured to include a measuring step of irradiating a surface of the crosslinked fluoropolymer resin with a laser to measure a Raman spectrum, and an acceptance or rejection decision step of determining an acceptance or a rejection of a quality of a measurement region irradiated with the laser, on the basis of an intensity of a fluorescence spectrum relative to an intensity of a Raman scattering peak, which is ascribed to a $CF_2$ stretching vibration, in the measured Raman spectrum.

5 Claims, 10 Drawing Sheets

(56) References Cited

FOREIGN PATENT DOCUMENTS

WO    WO 2016/093180 A1 *  6/2016  ............. G01N 30/88

OTHER PUBLICATIONS

WO 2016/093180 A1 (Jun. 16, 2016); machine translation. (Year: 2016).*
JP 2003-253007 A (Sep. 10, 2003); machine translation. (Year: 2003).*
Japanese Office Action, dated Feb. 14, 2023, in related Japanese Application No. 2020-010430 and English Machine Translation thereof.
"Surface Modification of Polymers by the Application of Plasma" ThreeBond Technical News, Japan, ThreeBond, Jan. 10, 1989, vol. 26, pp. 1-10 and its partial English translation.
Surface Modification of Polymers by the Application of Plasma "ThreeBond Technical News", Japan, ThreeBond, Jul. 10, 1989, vol. 26, pp. 1-10, and its partial English translation.
Japanese Office Action dated Jul. 11, 2023, in corresponding Japanese Patent Application No. 2020-010430, and English translation thereof.
Japanese Office Action, dated Feb. 6, 2024 in Japanese Application No. 2023-064874 and English Translation thereof.

* cited by examiner

CROSSLINKED FLUOROPOLYMER RESIN AND CONTROL METHOD FOR SAME

CROSS-REFERENCE TO RELATED APPLICATION

The present application is based on Japanese patent application No. 2020-010430 filed on Jan. 24, 2020, the entire contents of which are incorporated herein by reference.

BACKGROUND OF THE INVENTION

1. Field of the Invention

The present invention relates to a crosslinked fluoropolymer resin and a control method for the same crosslinked fluoropolymer resin.

2. Description of the Related Art

Conventionally, a technique for suppressing the occurrence of a discoloration in molding of a fluoropolymer resin modified by being irradiated with a radiation has been known (see JP2003-253007A). According to JP2003-253007A, by subjecting the fluoropolymer resin irradiated with the predetermined dose of radiation to a heat treatment of 50 degrees C. or higher, it is possible to suppress the occurrence of a discoloration in the fluoropolymer resin being molded by hot molding, and thereby maintain the inherent clean image of the fluoropolymer resin.

[Patent Document 1] JP2003-253007A

SUMMARY OF THE INVENTION

The cause of the occurrence of a discoloration in the modified fluoropolymer resin has been thought to be a defect formation resulting from the irradiation with the radiation. However, even when a visual decision on the presence or absence of the discoloration in the modified fluoropolymer resin has been able to be made, no visual confirmation of the presence or absence of the defect formation in a micro region of the modified fluoropolymer resin that has not been caused to appear as the discoloration has been able to be made. That is, the fluoropolymer resin with no discoloration caused therein produced with the technique disclosed by JP2003-253007A has been subjected to the defect formation that can cause the discoloration of the fluoropolymer resin and, as a result, there has been concern that the aforementioned defect formation caused in the fluoropolymer resin may adversely affect the properties of the fluoropolymer resin.

It is an object of the present invention to provide a control method for a crosslinked fluoropolymer resin, which is designed to determine the presence or absence of a micro defect formation that can be caused in the crosslinked fluoropolymer resin by irradiation with a radiation, but which cannot be visually identified, and it is another object of the present invention to provide the crosslinked fluoropolymer resin, from which the micro defect formation resulting from the irradiation with the radiation has been removed by use of the same control method for the crosslinked fluoropolymer resin.

For the purpose of solving the above described problem, the present invention provides a quality control method for a crosslinked fluoropolymer resin, comprising: a measuring step of irradiating a surface of the crosslinked fluoropolymer resin with a laser to measure a Raman spectrum; and an acceptance or rejection decision step of determining an acceptance or a rejection of a quality of a measurement region irradiated with the laser, on basis of an intensity of a fluorescence spectrum relative to an intensity of a Raman scattering peak, which is ascribed to a $CF_2$ stretching vibration, in the measured Raman spectrum.

(Points of the Invention)

According to the present invention, it is possible to provide the control method for the crosslinked fluoropolymer resin, which is designed to determine the presence or absence of a micro defect formation that can be caused in the crosslinked fluoropolymer resin by irradiation with a radiation, but which cannot be visually identified, and it is possible to provide the crosslinked fluoropolymer resin, from which the micro defect formation resulting from the irradiation with the radiation has been removed by use of the same control method for the crosslinked fluoropolymer resin.

BRIEF DESCRIPTION OF THE DRAWINGS

Next, the embodiment of the present invention will be described in accordance with appended drawings.

DETAILED DESCRIPTION OF THE PREFERRED EMBODIMENTS

Figure 1:
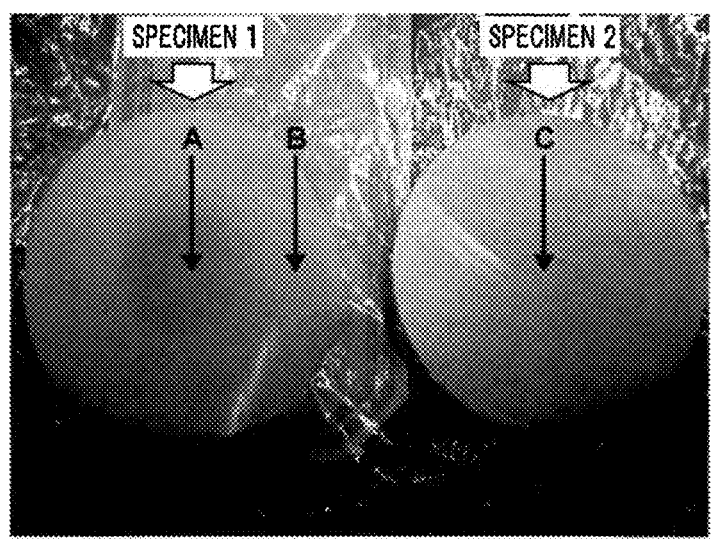
FIG. 1 is a photograph showing two states (left and right images) of a crosslinked PTFE, after heat treatments, respectively, in the left image of which a dull color portion has been formed adjacent to a center by irradiation with an electron beam.

First Embodiment (Properties of a Crosslinked Fluoropolymer Resin)

A fluoropolymer resin can be stabilized in its structure, by being crosslinked by being irradiated with a radiation. However, the fluoropolymer resin is low in its resistance to the radiation, and has been subjected to a defect formation and a subsequent discoloration, resulting from the irradiation with the radiation. There has been concern that the aforementioned defect formation caused in the fluoropolymer resin may adversely affect the properties of the fluoropolymer resin such as an abrasion resistance, a deformation performance, and the like. Hereinafter, the fluoropolymer resin crosslinked by the irradiation with the radiation will be referred to as the crosslinked fluoropolymer resin.

Examples of the aforementioned fluoropolymer resin include a poly tetrafluoro ethylene (PTFE), an ethylene tetrafluoro ethylene (ETFE), a polyfluoro alkoxy fluoropolymer resin (PFA), a tetrafluoro ethylene hexafluoro propylene copolymer (FEP), and mixtures thereof.

Examples of the radiation used in the crosslinking of the fluoropolymer resin include ionizing radiations such as an electron beam radiation, a γ-ray radiation, an X-ray radiation, a neutron beam radiation, a high energy ion beam radiation, and the like.

On the other hand, subjecting the crosslinked fluoropolymer resin to a heat treatment under predetermined conditions enables the crosslinked fluoropolymer resin to recover from the defect formation caused therein by the irradiation with the radiation. At this point of time, when the discoloration of the crosslinked fluoropolymer resin that has been caused to appear due to the defect formation caused therein has been dissipated by the heat treatment, it is possible to determine that the crosslinked fluoropolymer resin has recovered to some extent from the defect formation caused therein. However, even when the discoloration of the crosslinked fluoropolymer resin has been dissipated by the heat treatment, the micro defect formation caused therein that has not been caused to appear as the discoloration has remained to be dissipated.

(Quality Control Method for the Crosslinked Fluoropolymer Resin)

A quality control method for the crosslinked fluoropolymer resin according to the present embodiment is designed to use the Raman scattering intensity measurement, to make a decision on the presence or absence of a defect formation that can be caused in the crosslinked fluoropolymer resin by the irradiation with the radiation. In the Raman scattering intensity measurement, since a spot diameter of a laser with which the surface of the crosslinked fluoropolymer resin is irradiated serves as a measurement region, it is possible to make a decision on the presence or absence of the defect formation within a micro region of from several μm to several tens of μm on the surface of the crosslinked fluoropolymer resin. Here, in order to make it as easy as possible to find the defect formation in the crosslinked fluoropolymer resin, or in order to carry out a mapping, which will be described later, it is preferable to carry out the decision making on the presence or absence of the defect formation on the crosslinked fluoropolymer resin molded into a sheet shape.

FIG. 1 is a photograph showing two states (left and right images) of the crosslinked PTFE after the heat treatments, respectively, of the crosslinked PTFE, in the left image of which a dull color portion has been formed adjacent to a center by irradiation with an electron beam. In the left side of FIG. 1 is shown the crosslinked PTFE (also referred to as the specimen 1) that has been subjected to the heat treatment in an atmosphere at 315 degrees C. for 18 hours. In the right side of FIG. 1 is shown the crosslinked PTFE (also referred to as the specimen 2) that has been subjected to the heat treatment in an atmosphere at 315 degrees C. for 45 hours. By a visual comparison of the states of the specimen 1 and the specimen 2, it has been able to be confirmed that the brownish discolored portion remaining adjacent to the center after the heat treatment at 315 degrees C. for 18 hours has been dissipated after the heat treatment at 315 degrees C. for 45 hours.

Figure 2:
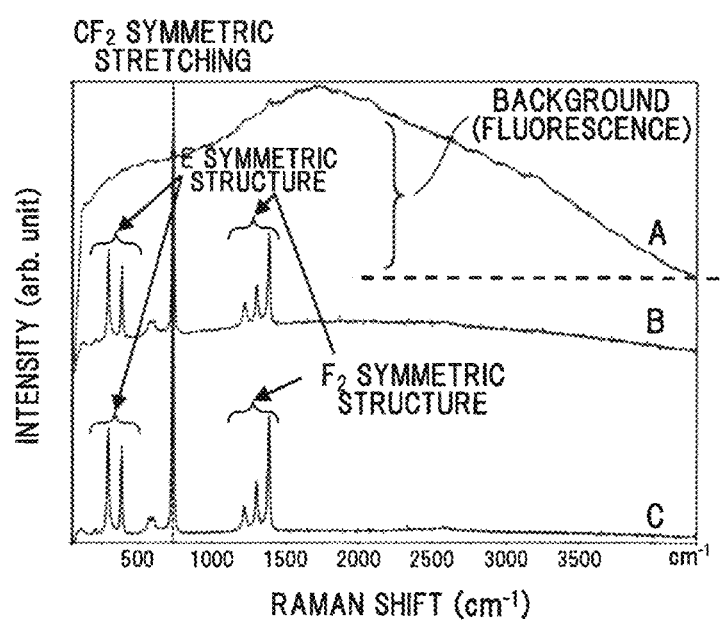
FIG. 2 shows Raman spectra measured by irradiation of measurement points A and B on a specimen 1 and a measurement point C on a specimen 2, respectively, shown in FIG. 1 with a laser.

FIG. 2 shows Raman spectra measured by irradiation of measurement points A and B on the specimen 1 and a measurement point C on the specimen 2, respectively, shown in FIG. 1 with a laser. The Raman scattering intensity measurement to obtain the spectra shown in FIG. 2 has used the RAMANforce Standard VIS-NIR-HS available from Nanophoton Corporation, and has been conducted in the following conditions: the laser wavelength has been 532 nm, the width of the entrance slit of the spectroscope has been 50 μm, the number of ruled grating grooves of the diffraction grating has been 300 gr/mm, the value of the ratio (attenuation ratio) of the amount of the laser light after attenuation to the maximum amount of the laser light of an ND (Neutral Density) filter has been 150/255, and the measurement temperature has been 26 degrees C.

In the measured Raman spectrum at the measurement point A included in the discolored portion, a broad fluorescence spectrum has been identified. The fluorescence spectrum has been observed as a large background in the measured Raman spectrum for the crosslinked PTFE, and many of the Raman scattering peaks in the measured Raman spectrum for the crosslinked PTFE have been buried in the fluorescence spectrum.

The Raman spectrum at the measurement point B, which has been a point at which no discoloration in the specimen 1 has been observed, has been weak in the fluorescence spectrum, as compared with the measured Raman spectrum at the measurement point A. Further, it has been able to be confirmed that the fluorescence spectrum has been weaker, in the measured Raman spectrum at the measurement point C in the specimen 2, which has been a point at which the discoloration observed in the specimen 1 has been dissipated by the heat treatment at 315 degrees C. for 45 hours. From these facts, it has been seen that the fluorescence spectrum has been identified in the discolored portion of the crosslinked fluoropolymer resin.

The inventors of the present application have found out from a research including the above experiment that the larger the number of defect formations resulting from the irradiation with the radiation within the measurement region in the Raman scattering intensity measurement of the crosslinked fluoropolymer resin, the higher the intensity of the fluorescence spectrum in the measured Raman spectrum. In addition, the inventors of the present application have established a method of knowing the amount of the defect formations by obtaining the intensity of the fluorescence spectrum with reference to the intensity of the Raman scattering peak, which is ascribed to a $CF_2$ stretching vibration, and which is the highest in the Raman scattering intensity in the measured Raman spectrum of the crosslinked fluoropolymer resin. The Raman scattering peak, which is ascribed to the $CF_2$ stretching vibration, is a maximum Raman scattering intensity within a wave number range of not smaller than 705 $cm^{-1}$ and not larger than 760 $cm^{-1}$, in the measured Raman spectrum.

The quality control method for the crosslinked fluoropolymer resin according to the present embodiment is configured to include a measuring step of irradiating a surface of the crosslinked fluoropolymer resin with a laser to measure a Raman spectrum; and an acceptance or rejection decision step of determining an acceptance or a rejection of a quality of a measurement region irradiated with the laser, on the basis of an intensity of a fluorescence spectrum relative to an intensity of a Raman scattering peak, which is ascribed to a $CF_2$ stretching vibration, in the measured Raman spectrum.

Figure 3A:
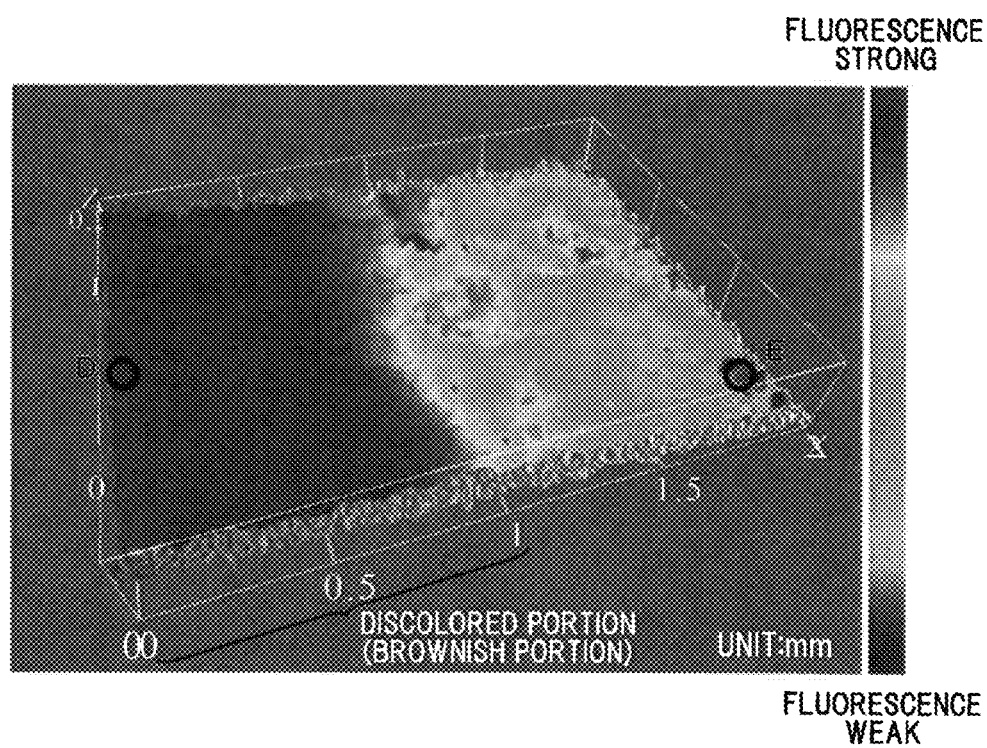
FIG. 3A shows a mapping image for a fluorescence intensity measured by the Raman scattering intensity measurement in an area of approximately 2 mm×1.5 mm adjacent to the boundary of the discolored portion of the specimen 1.

FIG. 3A shows a mapping image for the fluorescence intensity measured by the Raman scattering intensity measurement in an area of approximately 2 mm×1.5 mm adjacent to the boundary of the discolored portion of the specimen 1. The substantially left half region in FIG. 3A has been the discolored portion of the specimen 1, in which, overall, a strong fluorescence intensity has been identified. On the other hand, the right half region in FIG. 3A has been a region of the specimen 1 in which no discoloration has been observed, and it has been confirmed that most of that region of the specimen 1 have been weaker in the fluorescence intensity than the discolored portion of the specimen 1.

The Raman scattering intensity measurement to obtain the mapping image shown in FIG. 3A has used the RAMAN-force Standard VIS-NIR-HS available from Nanophoton Corporation, and has been conducted in the following conditions: the laser wavelength has been 785 nm, the width of the entrance slit of the spectroscope has been 50 μm, the number of ruled grating grooves of the diffraction grating has been 300 gr/mm, the attenuation ratio of the ND (Neutral Density) filter has been 220/255, and the measurement temperature has been 26 degrees C. In addition, the mapping condition has been set at 1 cycle/1 pixel (20 μm/1 pixel).

Figure 3B:
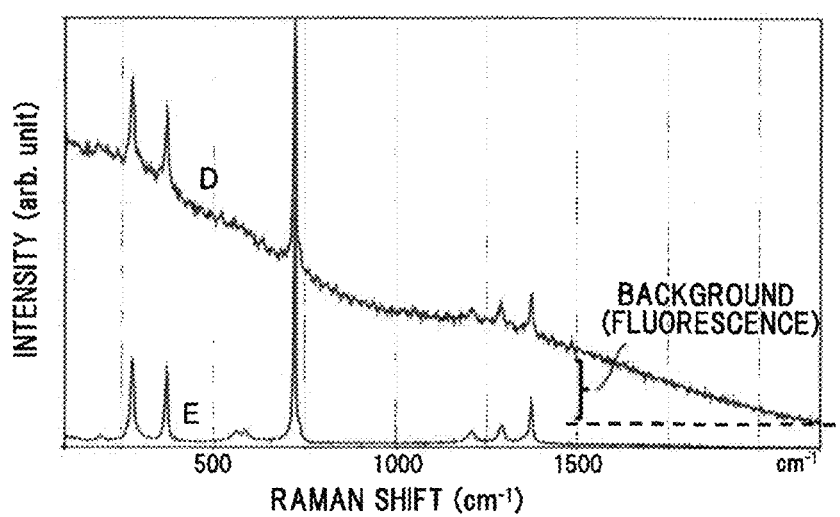
FIG. 3B shows Raman spectra at a measurement point D and a measurement point E, respectively, on the mapping image shown in FIG. 3A.

FIG. 3B shows Raman spectra at a measurement point D and a measurement point E, respectively, on the mapping image shown in FIG. 3A. The measurement point D has been a point which has been high in the fluorescence intensity in the discolored portion of the specimen 1, while the measurement point E has been a point which has been low in the fluorescence intensity in a portion of the specimen 1 in which no discoloration has been observed. By a comparison of the measured Raman spectrum at the measurement point D with the measured Raman spectrum at the measurement point A shown in FIG. 2, the fluorescence spectrum at the measurement point D has likewise been identified, though the intensity thereof has been low due to the wavelength of the laser having been long. Note that the value of the ratio of the integrated intensity in a wave number range of from 767 to 794 $cm^{-1}$ of the fluorescence spectrum to the integrated intensity in a wave number range of from 705 to 760 $cm^{-1}$ of the $CF_2$ stretching vibration peak has not been dependent on the wavelengths of the laser (when the laser wavelengths have been 532 nm and 785 nm, the values of the above ratios, respectively, have remained unchanged).

Table 1 below shows the presence or absence of discolorations by visual observation of the measurement points A to E, the respective integrated intensities (in the column of integrated intensity $I_1$ in Table 1) in a wave number range of from 705 to 760 $cm^{-1}$ of the $CF_2$ stretching vibration peaks in the measured Raman spectra, the respective integrated intensities (in the column of integrated intensity $I_2$ in Table 1) in a wave number range of from 767 to 794 $cm^{-1}$ of the fluorescence spectra, the respective values of the ratios (in the column of $I_2/I_1$ in Table 1) of the respective integrated intensities $I_2$ to the respective integrated intensities $I_1$, and the respective wavelengths of the laser light source in the Raman scattering intensity measurement at the measurement points A to E. Note that the respective integrated intensities $I_1$ and the respective integrated intensities $I_2$ have been calculated by integrating the intensities of the measured Raman spectra containing the respective backgrounds without performing the background corrections for the measured Raman spectra.

TABLE 1

| Measurement point | Presence or absence of discoloration | Integrated intensity $I_1$ (arb. unit) | Integrated intensity $I_2$ (arb. unit) | $I_2/I_1$ | Laser light source wavelength (nm) |
| --- | --- | --- | --- | --- | --- |
| A | Present | 424031 | 420336 | 0.99 | 532 |
| B | Absent | 17760 | 6944 | 0.39 | 532 |
| C | Absent | 14036 | 2340 | 0.17 | 532 |
| D | Present | 75389 | 65988 | 0.88 | 785 |
| E | Absent | 16882 | 9144 | 0.54 | 785 |

Based on these results, in the quality control method for the crosslinked fluoropolymer resin according to the present embodiment described above, for example, in the above described acceptance or rejection decision step, if the value $I_2/I_1$ of the ratio of the integrated intensity $I_2$ in a wave number range of 767 to 794 $cm^{-1}$ of the fluorescence spectrum to the integrated intensity $I_1$ in a wave number range of 705 to 760 $cm^{-1}$ of the $CF_2$ stretching vibration peak is not more than 0.55, then the quality of the above described measurement region on the surface of the crosslinked fluoropolymer resin can be regarded as accepted.

Figure 4A:
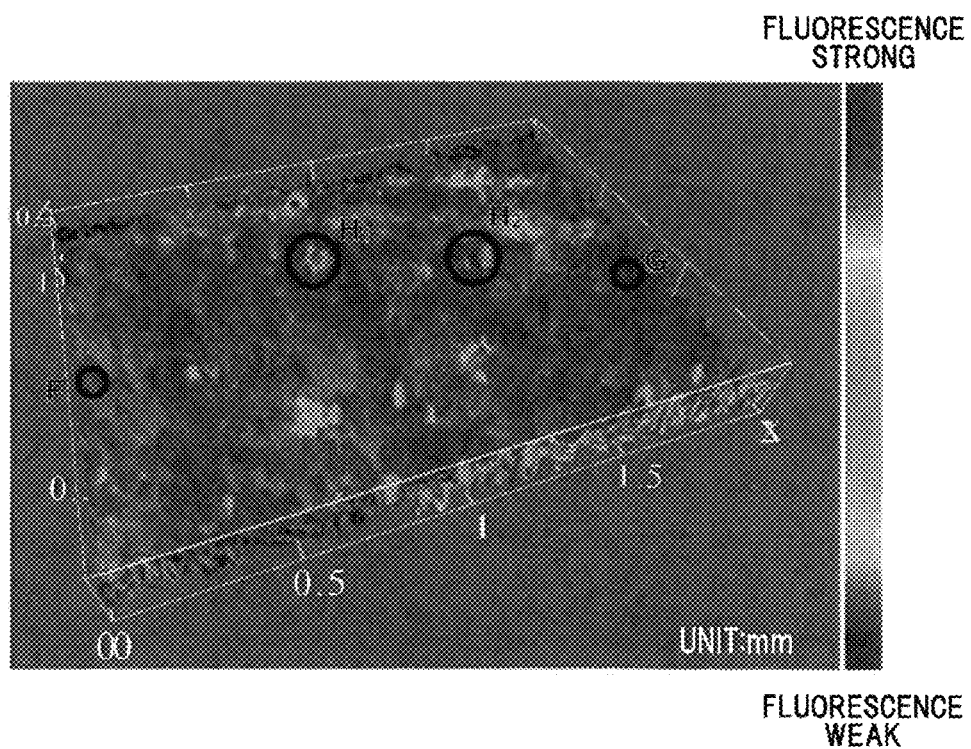
FIG. 4A shows a mapping image for a fluorescence intensity measured by the Raman scattering intensity measurement in an area of approximately 2 mm×1.5 mm adjacent to the boundary of the discolored portion of the specimen 2.

FIG. 4A shows a mapping image for the fluorescence intensity measured by the Raman scattering intensity measurement in an area of approximately 2 mm×1.5 mm adjacent to the boundary of the discolored portion of the specimen 2. As described above, in the specimen 2, the discoloration of the specimen 2 has been dissipated by the heat treatment, and the fluorescence intensity has been low over the entire region of the mapping area shown in FIG. 4A. Note that the conditions for the Raman scattering intensity measurement to obtain the mapping image shown in FIG.

4A have been the same as the conditions for the Raman scattering intensity measurement to obtain the mapping image shown in FIG. 3A.

Figure 4B:
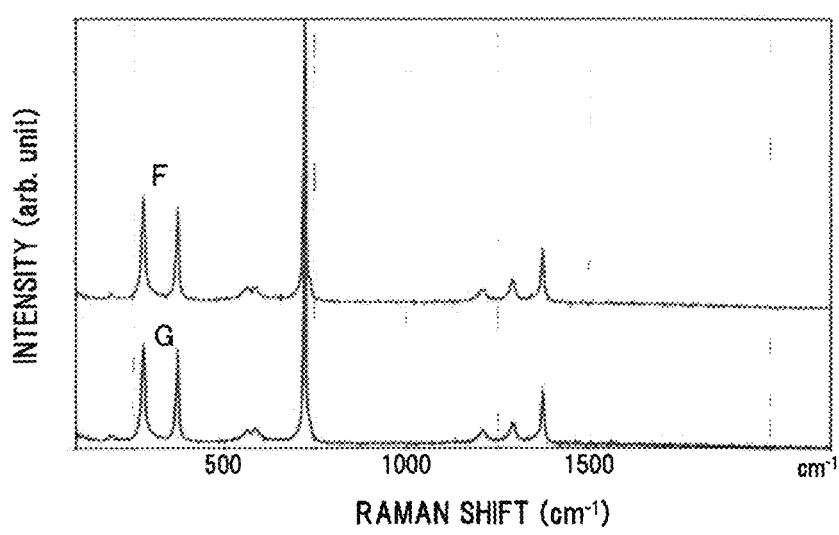
FIG. 4B shows Raman spectra at a measurement point F and a measurement point G, respectively, on the mapping image shown in FIG. 4A.

FIG. 4B shows Raman spectra at a measurement point F and a measurement point G, respectively, on the mapping image shown in FIG. 4A. The measurement point F and the measurement point G have been points at both of which no discoloration has been observed, and it has been confirmed that the intensities of the fluorescence spectra at the measurement point F and the measurement point G have been low.

On the other hand, from the mapping image shown in FIG. 4A, it has been able to be confirmed that micro regions (for example, circled regions $H_1$ and $H_2$) which have been high in the fluorescence intensity have been scattered. This has showed that even in the fluoropolymer resin whose discoloration has failed to be visually identified, there has been the micro defect formation caused by the irradiation with the radiation.

Figure 5A:
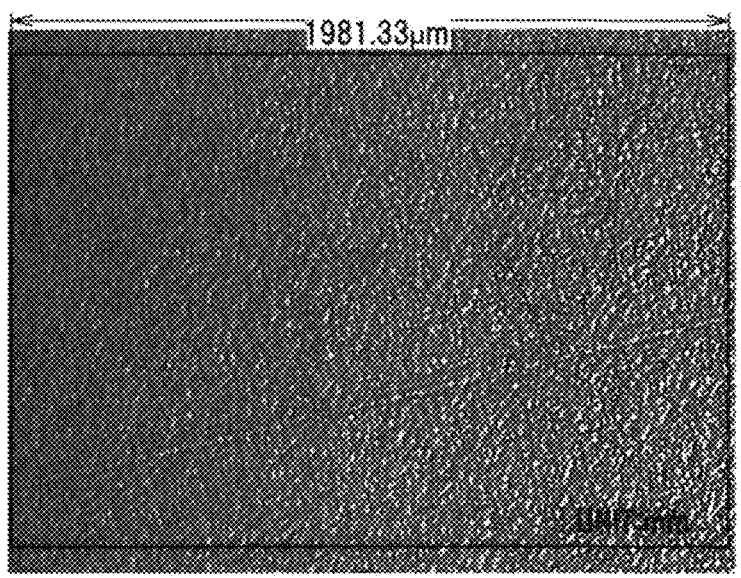
FIG. 5A shows an optical microscope image of the mapping area for the specimen 1 shown in FIG. 3A.
Figure 5B:
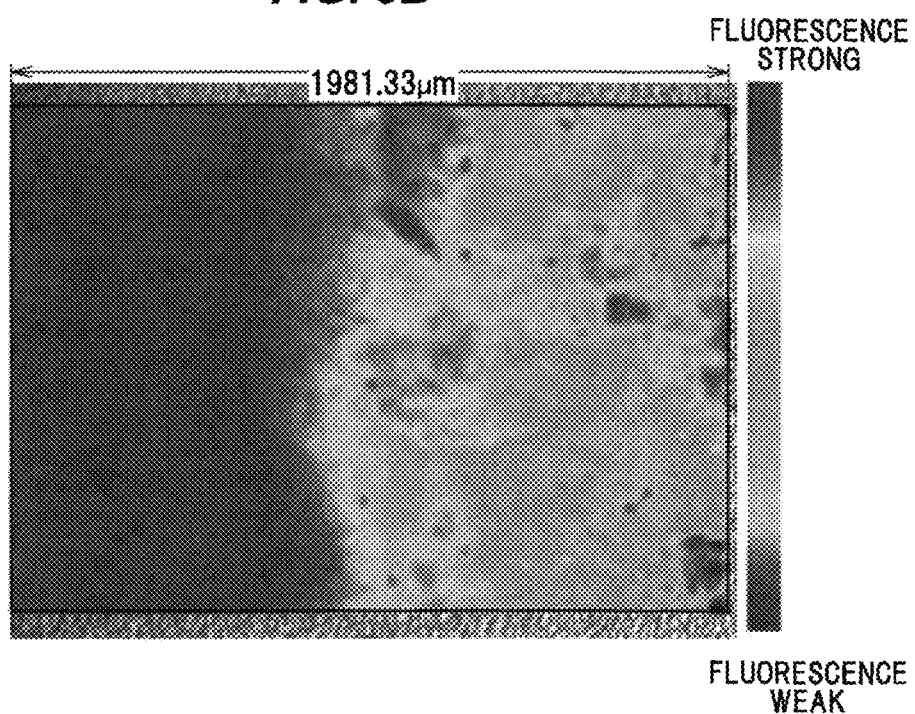
FIG. 5B shows a two-dimensional mapping image for the fluorescence intensity in the specimen 1 shown in FIG. 3A.
Figure 6A:
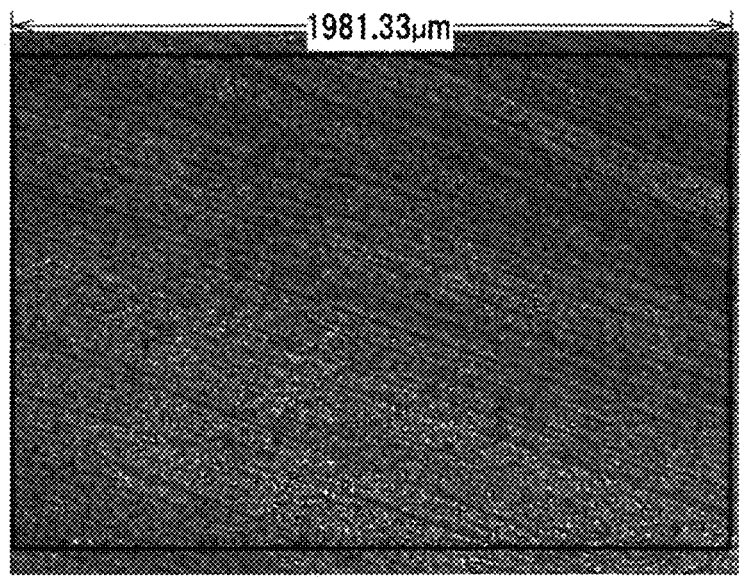
FIG. 6A shows an optical microscope image of the mapping area for the specimen 2 shown in FIG. 4A.
Figure 6B:
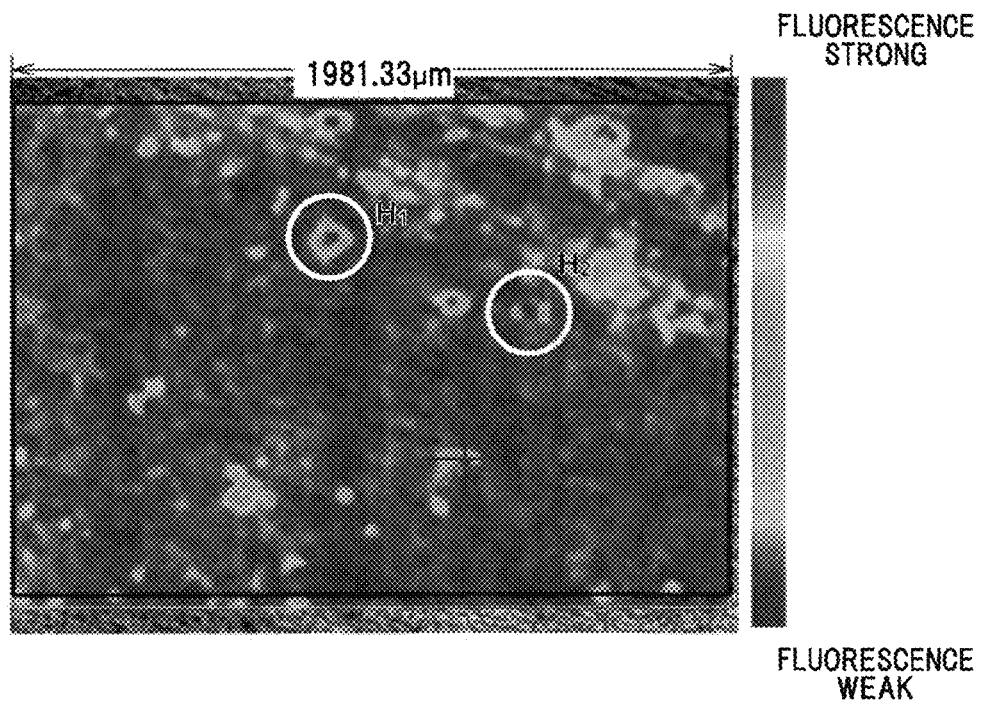
FIG. 6B shows a two-dimensional mapping image for the fluorescence intensity in the specimen 2 shown in FIG. 4A.

FIG. 5A shows an optical microscope image of the mapping area for the specimen 1 shown in FIG. 3A, while FIG. 5B shows a two-dimensional mapping image for the fluorescence intensity in the specimen 1 shown in FIG. 3A. FIG. 6A shows an optical microscope image of the mapping area for the specimen 2 shown in FIG. 4A, while FIG. 6B shows a two-dimensional mapping image for the fluorescence intensity in the specimen 2 shown in FIG. 4A.

The quality control method for the crosslinked fluoropolymer resin according to the present embodiment is able to make a decision on the presence or absence of the defect formation within the micro region on which no visual decision can be made by the presence or absence of the discoloration, by the use of the Raman scattering intensity measurement. In addition, when the presence of the defect formation within the micro region has been identified, the above quality control method subjects the crosslinked fluoropolymer resin to a further heat treatment to allow the crosslinked fluoropolymer resin to recover from the defect formation, or scrapes the defect formation containing portion of the crosslinked fluoropolymer resin, thereby being able to produce the crosslinked fluoropolymer resin with substantially no micro defect formation contained therein.

That is, the quality control method for the crosslinked fluoropolymer resin according to the present embodiment may be configured in such a manner as to include a step of removing the measurement region, which has been regarded as rejected in the above described acceptance or rejection decision step, or a step of subjecting the crosslinked fluoropolymer resin to a heat treatment, to upgrade the quality of the above described measurement region, which has been regarded as rejected in the above described acceptance or rejection decision step, to the quality to be regarded as accepted.

(Crosslinked Fluoropolymer Resin)

As described above, the quality control method for the crosslinked fluoropolymer resin according to the present embodiment detects the micro defect formation caused in the crosslinked fluoropolymer resin, and allows the crosslinked fluoropolymer resin to recover from the detected micro defect formation, or removes the detected micro defect formation, thereby being able to produce the crosslinked fluoropolymer resin with substantially no micro defect formation contained therein.

An example is given in which, in the above described acceptance or rejection decision step of the quality control method for the crosslinked fluoropolymer resin according to the present embodiment, an acceptance decision is made on the quality of the above described measurement region on the surface of the crosslinked fluoropolymer resin when the value of the ratio of the integrated intensity in a wave number range of 767 to 794 $cm^{-1}$ of the fluorescence spectrum to the integrated intensity in a wave number range of 705 to 760 $cm^{-1}$ of the $CF_2$ stretching vibration peak is not more than 0.55, and in this case, it is possible to produce the crosslinked fluoropolymer resin which is configured in such a manner that when the Raman spectrum is measured by irradiating any part of the surface of the crosslinked fluoropolymer resin with a laser, the value of the ratio of the integrated intensity in a wave number range of 767 to 794 $cm^{-1}$ of the fluorescence spectrum to the integrated intensity in a wave number range of 705 to 760 $cm^{-1}$ of the Raman scattering peak, which is ascribed to the $CF_2$ stretching vibration in the measured Raman spectrum, is not more than 0.55.

The crosslinked fluoropolymer resin from which the micro defect formation has been removed is worked into a circular columnar bulk or sheet shape, and is used for a material for a tube, a hose, a packing, a sliding member, or an insulating member that is required to have heat resistance and corrosion resistance. Further, the above crosslinked fluoropolymer resin can also be used for a material for a medical part such as a blood analysis line tube, a catheter inner tube, an endoscope solution sending tube, or the like, which is in particular required to have no discoloration therein. Further, the above crosslinked fluoropolymer resin can also be used for a material for a positioning jig, a transfer jig, a chemical storage tank, or the like, in a semiconductor production line. The aforementioned positioning jig is, for example, a jig for positioning a large number of silicon wafers or the like in a hydrofluoric acid dipping step for the purpose of removing oxide films on the wafer surfaces of the silicon wafers, and the aforementioned transfer jig is, for example, a jig for transferring the large number of silicon wafers between steps, and these jigs are required to be resistant to the hydrofluoric acid (HF), and therefore the crosslinked fluoropolymer resin according to the present embodiment is suitable for the materials for these jigs.

Second Embodiment

A second embodiment of the present invention is different from the first embodiment in the defect formation measuring means used in the quality control method for the crosslinked fluoropolymer resin. Hereinafter, in the second embodiment, the same points as in the first embodiment will be omitted or simplified.

(Quality Control Method for the Crosslinked Fluoropolymer Resin)

A quality control method for the crosslinked fluoropolymer resin according to the second embodiment is designed to use the X-ray diffraction intensity measurement, to make a decision on the presence or absence of the defect formation resulting from the irradiation of the crosslinked fluoropolymer resin with the radiation. In the X-ray diffraction intensity measurement, since a spot diameter of an X-ray with which the surface of the crosslinked fluoropolymer resin is irradiated serves as a measurement region, it is possible to make a decision on the presence or absence of the defect formation within a micro region of approximately several hundreds of μm on the surface of the crosslinked fluoropolymer resin.

Figure 7A:
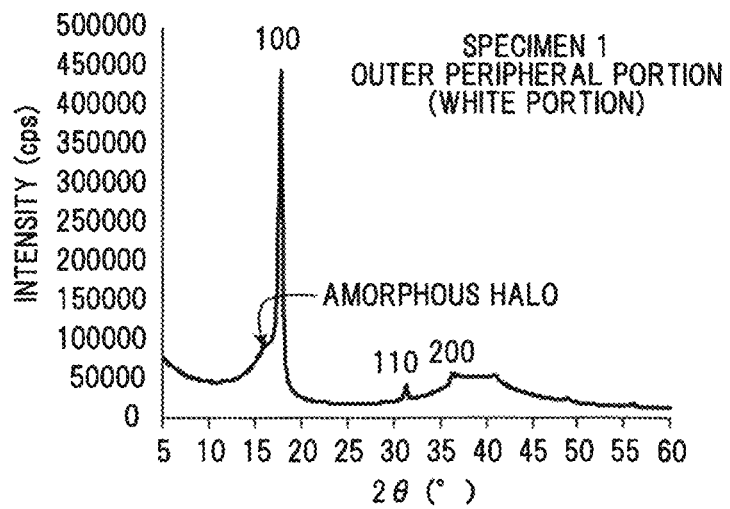
FIG. 7A shows an X-ray diffraction pattern of an outer peripheral portion with no discoloration caused therein in the specimen 1 shown in FIG. 1.
Figure 7B:
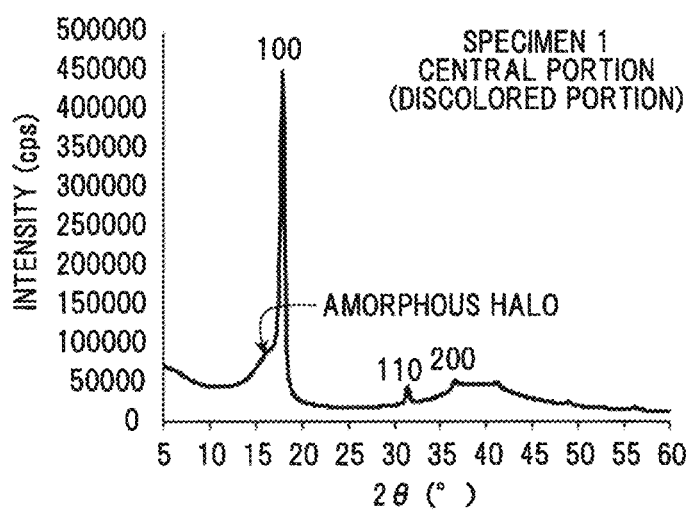
FIG. 7B shows an X-ray diffraction pattern of a central portion with a discoloration caused therein in the specimen 1 shown in FIG. 1.
Figure 8A:
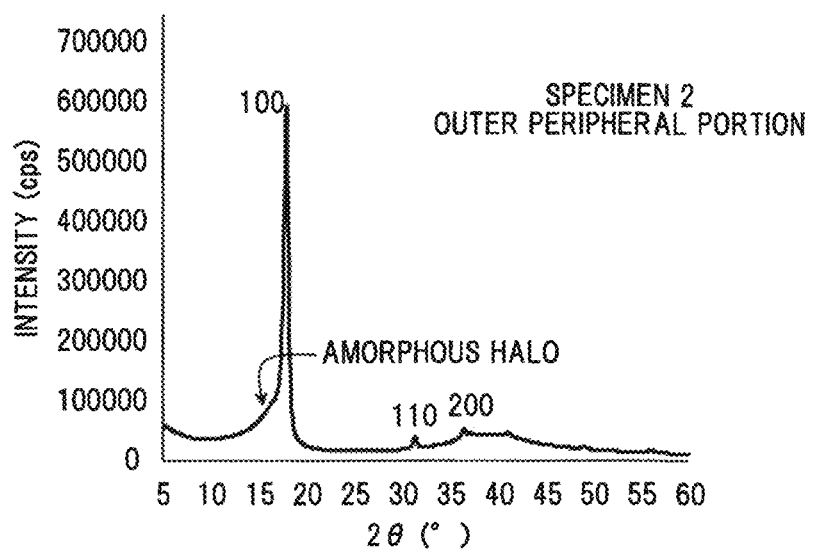
FIG. 8A shows an X-ray diffraction pattern of an outer peripheral portion with no discoloration caused therein in the specimen 2 shown in FIG. 1.
Figure 8B:
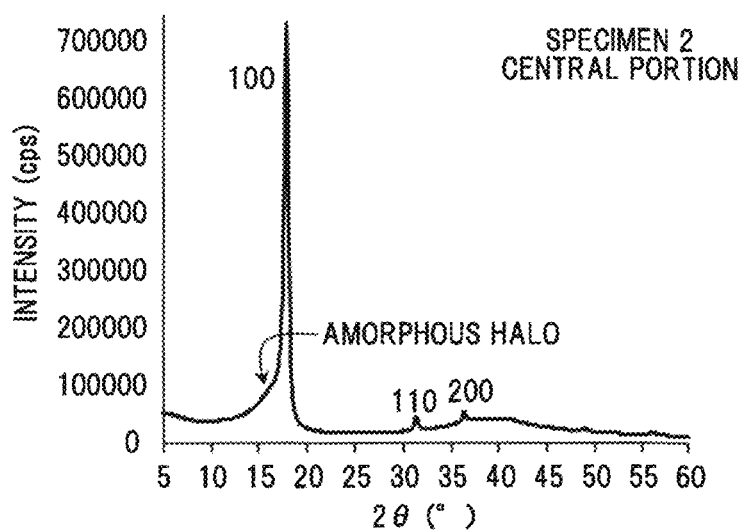
FIG. 8B shows an X-ray diffraction pattern of a central portion with no discoloration caused therein in the specimen 2 shown in FIG. 1.

FIG. 7A shows an X-ray diffraction pattern of an outer peripheral portion with no discoloration caused therein in the specimen 1 shown in FIG. 1, while FIG. 7B shows an X-ray diffraction pattern of a central portion with a discoloration caused therein in the specimen 1 shown in FIG. 1. FIG. 8A shows an X-ray diffraction pattern of an outer peripheral portion with no discoloration caused therein in the specimen 2 shown in FIG. 1, while FIG. 8B shows an X-ray diffraction pattern of a central portion with no discoloration caused therein in the specimen 2 shown in FIG. 1. For these X-ray diffraction intensity measurements, a CuKα ray having a wavelength of 0.1541838 nm has been used as the X-ray. The measurement temperature has been 26 degrees C.

In each of the above X-ray diffraction patterns shown in FIGS. 7A, 7B, 8A and 8B, each amorphous halo due to scattered light due to amorphousness has appeared at each shoulder on the low angle side of each diffraction peak from (100) planes.

Figure 9A:
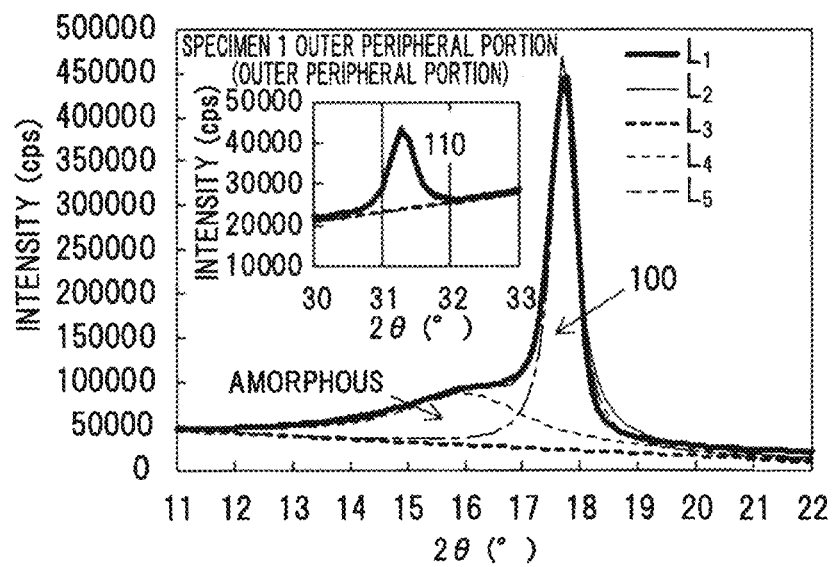
FIG. 9A shows diffraction peaks corresponding to (100) plane and (110) plane and an amorphous scattering, which have been resolved by the fitting analysis of the X-ray diffraction pattern shown in FIG. 7A.
Figure 9B:
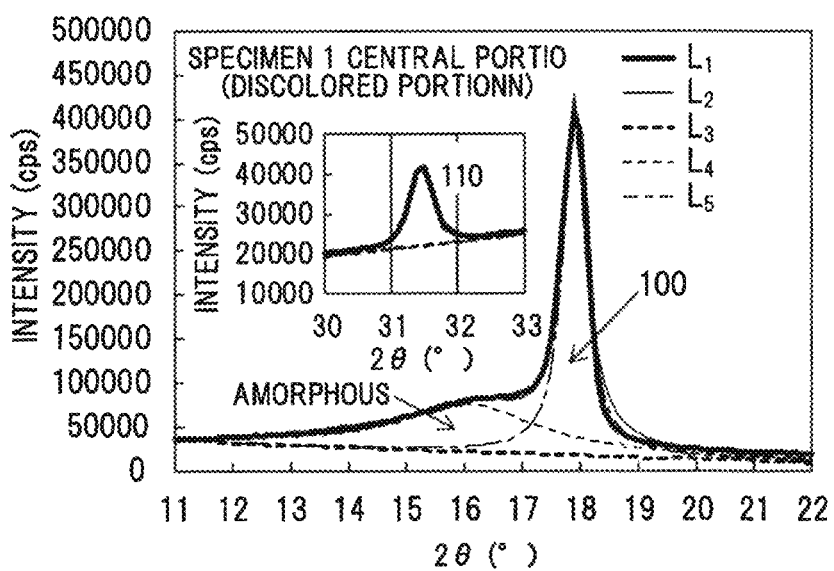
FIG. 9B shows diffraction peaks corresponding to (100) plane and (110) plane and an amorphous scattering, which have been resolved by the fitting analysis of the X-ray diffraction pattern shown in FIG. 7B.
Figure 10A:
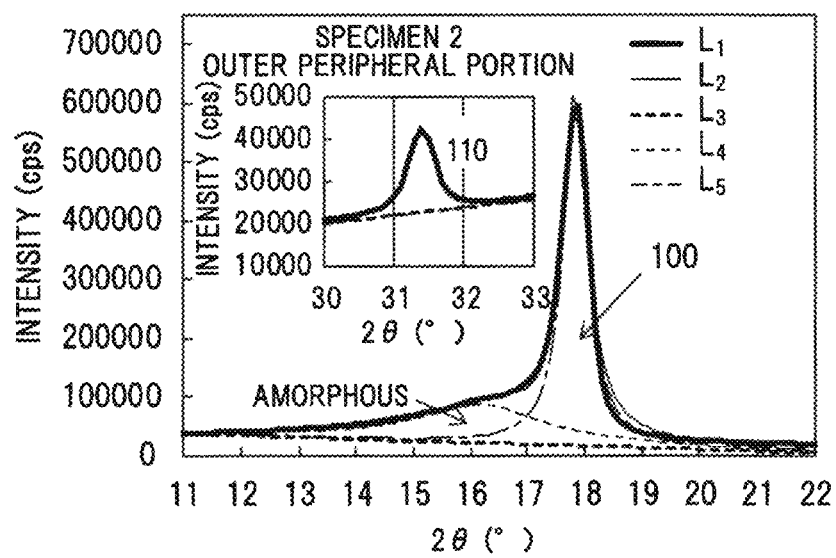
FIG. 10A shows diffraction peaks corresponding to (100) plane and (110) plane and an amorphous scattering, which have been resolved by the fitting analysis of the X-ray diffraction pattern shown in FIG. 8A.
Figure 10B:
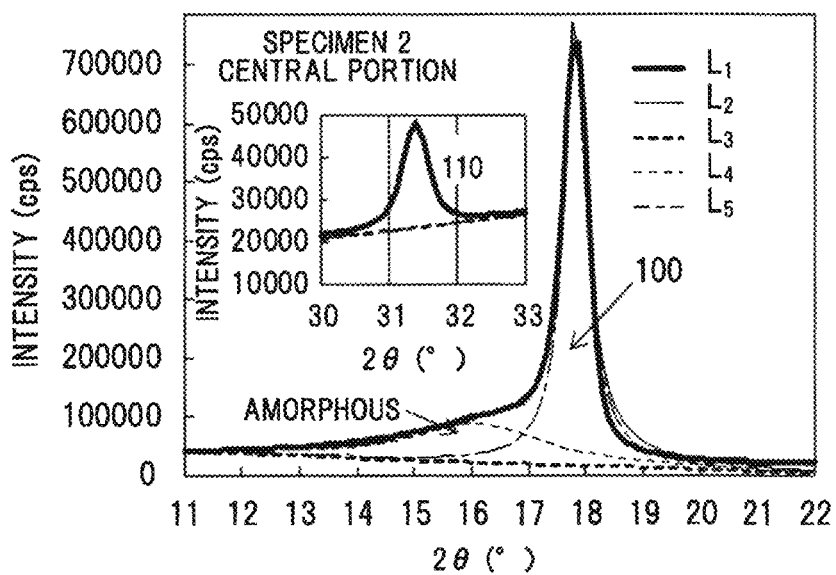
FIG. 10B shows diffraction peaks corresponding to (100) plane and (110) plane and an amorphous scattering, which have been resolved by the fitting analysis of the X-ray diffraction pattern shown in FIG. 8B.

FIG. 9A shows the diffraction peak from the (100) and (110) planes and the amorphous scattering, which have been resolved by the fitting analysis of the X-ray diffraction pattern shown in FIG. 7A, while FIG. 9B shows the diffraction intensity peak from the (100) and (110) planes and the amorphous scattering, which have been resolved by the fitting analysis of the X-ray diffraction pattern shown in FIG. 7B. FIG. 10A shows the diffraction peak from the (100) planes and the amorphous scattering, which have been resolved by the fitting analysis of the X-ray diffraction pattern shown in FIG. 8A, while FIG. 10B shows the diffraction peak from the (100) planes and the amorphous scattering, which have been resolved by the fitting analysis of the X-ray diffraction pattern shown in FIG. 8B. Here, the fitting analysis has been carried out by using the Lorentzian distribution function.

In each of FIGS. 9A, 9B, 10A and 10B, $L_1$ denotes each measured X-ray diffraction pattern line, $L_2$ denotes each fitting line, $L_3$ denotes each background line, $L_4$ denotes each resolved amorphous scattering line, and $L_5$ denotes each resolved diffraction peak line from the respective (100) planes.

Table 2 below shows, for each of the outer peripheral portion and the central portion of the specimen 1 and the outer peripheral portion and the central portion of the specimen 2, each spacing d between adjacent (100) lattice planes, each spacing d between adjacent (110) lattice planes, each degree of crystallinity, and each degree of (100) preferred orientation obtained from the X-ray diffraction patterns shown in FIGS. 9A, 9B, 10A and 10B.

TABLE 2

|  | Position of measurement point | Spacing d (nm) between adjacent (100) lattice planes | Spacing d (nm) between adjacent (100) lattice planes | Degree of crystallinity | Degree of (100) preferred orientation |
|---|---|---|---|---|---|
| Specimen 1 | Outer peripheral portion | 0.5003 | 0.2857 | 61% | 0.966 |
|  | Central portion | 0.4962 | 0.2845 | 54% | 0.952 |
| Specimen 2 | Outer peripheral portion | 0.4972 | 0.2849 | 65% | 0.973 |
|  | Central portion | 0.4976 | 0.2851 | 70% | 0.973 |

Here, the respective spacings d between the adjacent (100) lattice planes and the respective spacings d between the adjacent (110) planes have each been calculated by using the Bragg's law. In addition, the respective degrees of crystallinity ($\chi_1$) have been calculated by using the formula (1) below, while the respective degrees of (100) preferred orientation ($\chi_2$) have been calculated by using the formula (2) below. In the formulas (1) and (2), $I_{100}$ has been the integrated intensity of the diffraction peak from the (100) planes, while $I_{110}$ has been the integrated intensity of the diffraction peak from the (110) planes, and $I_A$ has been the integrated intensity of the amorphous scattering.

[Formula 1]

$$\chi_1 = \frac{I_{100}}{I_{100} + I_A} \times 100 \quad \text{(Eq. 1)}$$

[Formula 2]

$$\chi_2 = \frac{I_{100}}{I_{100} + I_{110}} \quad \text{(Eq. 2)}$$

Table 2 has showed that, between the specimen 1 having the discolored portion therein, and the specimen 2 in which the discoloration has been dissipated by the heat treatment, there have been the variations in each of the positions of the measurement points between the respective spacings d between the adjacent (100) lattice planes, and between the respective spacings d between the adjacent (110) lattice planes, and the differences in the respective degrees of crystallinity, and in the respective degrees of (100) preferred orientation. For example, at the measurement points for the specimen 2 in Table 2, at which the specimen 2 has been considered to have sufficiently recovered from the defect formations by the heat treatment, the respective degrees of crystallinity have been not lower than 65%, and the respective degrees of (100) preferred orientation have been not lower than 0.97, while, at the measurement points for the specimen 1 in Table 2 at which the defect formations have been considered to have remained to be dissipated, the respective degrees of crystallinity have been lower than 65%, and the respective degrees of (100) preferred orientation have been lower than 0.97.

The inventors of the present application have found out from a research including the above described experiment that there have been tendencies that the larger the number of defect formations resulting from the irradiation with the radiation within the measurement region in the X-ray diffraction intensity measurement of the crosslinked fluoropolymer resin, the greater the variations between the respective spacings d between the adjacent (100) lattice planes or the respective spacings d between the adjacent (110) lattice planes obtained from the X-ray diffraction patterns, or the lower the respective degrees of crystallinity obtained from the X-ray diffraction patterns, or the lower the respective degrees of (100) preferred orientation obtained from the X-ray diffraction patterns, or the like. The above described tendencies have been thought to have been due to the presence of the defect formations leading to a lattice strain and a lowering in the crystallinity.

In addition, the inventors of the present application have established the quality control method for the crosslinked fluoropolymer resin, which has been configured in such a manner as to include a measuring step of irradiating a surface of the crosslinked fluoropolymer resin with an X-ray to measure an X-ray diffraction pattern; and an acceptance or rejection decision step of determining an acceptance or a rejection of a quality of a measurement region irradiated with the X-ray, on the basis of at least one of a difference in distribution between the spacings d between the adjacent lattice planes (a difference between a maximum value and a minimum value in the entire crosslinked fluoropolymer resin), the respective degrees of crystallinity, and the respective degrees of (100) preferred orientation, which have been obtained from the measured X-ray diffraction pattern.

For example, in the above acceptance or rejection decision step, if at least one of the difference in distribution between the spacings d between the adjacent (100) lattice planes being not greater than 0.0027 nm, the respective degrees of crystallinity being not lower than 65%, and the respective degrees of (100) preferred orientation being not lower than 0.97 is met, then the quality of the above described measurement region can be regarded as accepted.

As with the quality control method for the crosslinked fluoropolymer resin according to the first embodiment using the Raman scattering intensity measurement, the quality control method for the crosslinked fluoropolymer resin according to the second embodiment is able to make a decision on the presence or absence of the defect formation within the micro region on which no visual decision can be made by the presence or absence of the discoloration. In addition, by carrying out the mappings of the spacings d between the adjacent lattice planes, the respective degrees of crystallinity, and the respective degrees of (100) preferred orientation, it is possible to know the positions of the micro defect formations scattered on the crosslinked fluoropolymer resin. Further, when the presence of the defect formation within the micro region has been identified, the above quality control method subjects the crosslinked fluoropolymer resin to a further heat treatment to allow the crosslinked fluoropolymer resin to recover from the defect formation, or scrapes the defect formation containing portion of the crosslinked fluoropolymer resin, thereby being able to produce the crosslinked fluoropolymer resin with substantially no micro defect formation contained therein.

That is, the quality control method for the crosslinked fluoropolymer resin according to the second embodiment may be configured in such a manner as to include a step of removing the measurement region, which has been regarded as rejected in the above described acceptance or rejection decision step, or a step of subjecting the crosslinked fluoropolymer resin to a heat treatment, to upgrade the quality of the above described measurement region, which has been regarded as rejected in the above described acceptance or rejection decision step, to the quality to be regarded as accepted.

(Crosslinked Fluoropolymer Resin)

As described above, the quality control method for the crosslinked fluoropolymer resin according to the second embodiment detects the micro defect formation caused in the crosslinked fluoropolymer resin, and allows the crosslinked fluoropolymer resin to recover from the detected micro defect formation, or removes the detected micro defect formation, thereby being able to produce the crosslinked fluoropolymer resin with substantially no micro defect formation contained therein.

An example is given in which, in the above described acceptance or rejection decision step of the quality control method for the crosslinked fluoropolymer resin according to the second embodiment, an acceptance decision is made on the quality of the above described measurement region on the surface of the crosslinked fluoropolymer resin when at least one of the difference in distribution between the spacings d between the adjacent (100) lattice planes being not greater than 0.0027 nm, the degree of crystallinity being not lower than 65%, and the degree of (100) preferred orientation being not lower than 0.97 is met, and in this case, it is possible to produce the crosslinked fluoropolymer resin which is configured in such a manner that when the diffraction pattern is measured by irradiating any part of the surface of the crosslinked fluoropolymer resin with an X-ray, at least one of the difference in distribution between the spacings d between the adjacent (100) lattice planes being not greater than 0.0027 nm, the degree of crystallinity being not lower than 65%, and the degree of (100) preferred orientation being not lower than 0.97, which have been obtained from the measured X-ray diffraction pattern, is met.

The crosslinked fluoropolymer resin from which the micro defect formation has been removed is worked into a circular columnar bulk or sheet shape, and is used for a material for a tube, a hose, a packing, a sliding member, or an insulating member that is required to have heat resistance and corrosion resistance. Further, the above crosslinked fluoropolymer resin can also be used for a material for a medical part such as a blood analysis line tube, a catheter inner tube, an endoscope solution sending tube, or the like, which is in particular required to have no discoloration therein. Further, the above crosslinked fluoropolymer resin can also be used for a material for a positioning jig, a transfer jig, a chemical storage tank, or the like, in a semiconductor production line.

Advantageous Effects of the Embodiments

According to the present embodiments, it is possible to provide the control methods for the crosslinked fluoropolymer resin, which are designed to determine the presence or absence of the micro defect formation that can be caused in the crosslinked fluoropolymer resin by the irradiation with the radiation, but which cannot be visually identified. In addition, it is possible to provide the crosslinked fluoropolymer resin, which is designed to be excellent in its properties such as an abrasion resistance, a deformation performance, and the like, by the use of the same control methods for the crosslinked fluoropolymer resin to remove the micro defect formation caused in the crosslinked fluoropolymer resin by the irradiation with the radiation.

In particular, when the crosslinked fluoropolymer resin is used for a material for a micro sized part, it is important to produce the crosslinked fluoropolymer resin having few micro defect formations, because the micro defect formations have a great influence on the properties of the part.

In addition, the quality control method for a diisononyl phthalate, the producing method for a resin composition, and the like according to the present embodiments can also be applied to the development of materials using materials informatics (MI) for analyzing data by exploiting machine learning or artificial intelligence (AI) or the like.

SUMMARY OF THE EMBODIMENTS

Next, the technical ideas grasped from the present embodiments will be described.

[1] A quality control method for a crosslinked fluoropolymer resin, comprising: a measuring step of irradiating a surface of the crosslinked fluoropolymer resin with a laser to measure a Raman spectrum; and an acceptance or rejection decision step of determining an acceptance or a rejection of a quality of a measurement region irradiated with the laser, on basis of an intensity of a fluorescence spectrum relative to an intensity of a Raman scattering peak, which is ascribed to a $CF_2$ stretching vibration, in the measured Raman spectrum.

[2] The quality control method for the crosslinked fluoropolymer resin as defined in the above [1], wherein, in the aforementioned acceptance or rejection decision step, if a value of a ratio of an integrated intensity in a wave number range of 767 to 794 $cm^{-1}$ of the fluorescence spectrum to an integrated intensity in a wave number range of 705 to 760 $cm^{-1}$ of the $CF_2$ stretching vibration is not more than 0.55, then the quality of the aforementioned measurement region irradiated with the laser is regarded as accepted.

[3] A quality control method for a crosslinked fluoropolymer resin, comprising: a measuring step of irradiating a surface of the crosslinked fluoropolymer resin with an X-ray to measure an X-ray diffraction pattern; and an acceptance or rejection decision step of determining an acceptance or a rejection of a quality of a measurement region irradiated with the X-ray, on basis of at least one of a difference in distribution between spacings d between adjacent lattice planes, a degree of crystallinity, and a degree of (100) preferred orientation, which have been obtained from the measured X-ray diffraction pattern.

[4] The quality control method for the crosslinked fluoropolymer resin as defined in the above [3], wherein, in the aforementioned acceptance or rejection decision step, if at least one of the difference in distribution between the spacings d between the adjacent (100) lattice planes being not greater than 0.0027 nm, the degree of crystallinity being not lower than 65%, and the degree of (100) preferred orientation being not lower than 0.97 is met, then the quality of the aforementioned measurement region irradiated with the X-ray is regarded as accepted.

[5] The quality control method for the crosslinked fluoropolymer resin as defined in any one of the above [1] to [4], further comprising a step of removing the aforementioned measurement region, which has been regarded as rejected in the aforementioned acceptance or rejection decision step, or a step of subjecting the crosslinked fluoropolymer resin to a heat treatment, to upgrade the quality of the aforementioned measurement region, which has been regarded as rejected in the aforementioned acceptance or rejection decision step, to a quality to be regarded as accepted.

[6] A crosslinked fluoropolymer resin, being configured in such a manner that when a Raman spectrum is measured by irradiating any part of a surface of the crosslinked fluoropolymer resin with a laser, a value of a ratio of an integrated intensity in a wave number range of 767 to 794 $cm^{-1}$ of a fluorescence spectrum to an integrated intensity in a wave number range of 705 to 760 $cm^{-1}$ of a Raman scattering peak which is ascribed to a $CF_2$ stretching vibration in the measured Raman spectrum, is not more than 0.55.

[7] A crosslinked fluoropolymer resin, being configured in such a manner that when an X-ray diffraction pattern is measured by irradiating any part of a surface of the crosslinked fluoropolymer resin with an X-ray, at least one of a difference in distribution between spacings d between adjacent (100) lattice planes being not greater than 0.0027 nm, a degree of crystallinity being not lower than 65%, and a degree of (100) preferred orientation being not lower than 0.97, which have been obtained from the measured X-ray diffraction pattern, is met.

Although the embodiments of the present invention have been described above, the present invention is not limited to the present embodiments, but various modifications can be made without departing from the spirit of the invention. In addition, the present embodiments are not to be construed as limiting the inventions according to the appended claims. In addition, it should be noted that not all the combinations of the features described in the embodiments are indispensable to the means for solving the problem of the invention.

Although the invention has been described relative to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A quality control method for a crosslinked fluoropolymer resin, comprising:
   a measuring step of irradiating a surface of the crosslinked fluoropolymer resin with a laser to measure a Raman spectrum; and
   an acceptance or rejection decision step of determining an acceptance or a rejection of a quality of a measurement region irradiated with the laser, on basis of an intensity of a fluorescence spectrum relative to an intensity of a Raman scattering peak, which is ascribed to a $CF_2$ stretching vibration, in a measured Raman spectrum.

2. The quality control method for the crosslinked fluoropolymer resin according to claim 1, wherein, in the acceptance or rejection decision step, if a value of a ratio of an integrated intensity in a wave number range of 767 to 794 $cm^{-1}$ of the fluorescence spectrum to an integrated intensity in a wave number range of 705 to 760 $cm^{-1}$ of the $CF_2$ stretching vibration is not more than 0.55, then the quality of the measurement region irradiated with the laser is regarded as accepted.

3. A quality control method for a crosslinked fluoropolymer resin, comprising:
   a measuring step of irradiating a surface of the crosslinked fluoropolymer resin with an X-ray to measure an X-ray diffraction pattern; and
   an acceptance or rejection decision step of determining an acceptance or a rejection of a quality of a measurement region irradiated with the X-ray, on basis of at least one of a difference in distribution between spacings d between adjacent lattice planes, a degree of crystallinity, and a degree of (100) preferred orientation, which have been obtained from a measured X-ray diffraction pattern.

4. The quality control method for the crosslinked fluoropolymer resin according to claim 3, wherein, in the acceptance or rejection decision step, if at least one of the difference in distribution between the spacings d between the adjacent (100) lattice planes being not greater than nm, the degree of crystallinity being not lower than 65%, and the degree of (100) preferred orientation being not lower than 0.97 is met, then the quality of the measurement region irradiated with the X-ray is regarded as accepted.

5. The quality control method for the crosslinked fluoropolymer resin according to claim 1, further comprising:
   a step of removing the measurement region, which has been regarded as rejected in the acceptance or rejection decision step, or a step of subjecting the crosslinked fluoropolymer resin to a heat treatment, to upgrade a quality of the measurement region, which has been regarded as rejected in the acceptance or rejection decision step, to a quality to be regarded as accepted.

* * * * *